United States Patent
Shiba et al.

(10) Patent No.: US 7,329,522 B2
(45) Date of Patent: Feb. 12, 2008

(54) POLYPHOSPHATE:AMP PHOSPHOTRANSFERASE

(75) Inventors: Toshikazu Shiba, Tokyo (JP); Toshitada Noguchi, Chiba (JP)

(73) Assignee: Yamasa Corporation, Choshi-shi (JP)

( * ) Notice: Subject to any disclaimer, the term of this patent is extended or adjusted under 35 U.S.C. 154(b) by 426 days.

(21) Appl. No.: 10/514,726

(22) PCT Filed: May 28, 2003

(86) PCT No.: PCT/JP03/06646

§ 371 (c)(1), (2), (4) Date: Nov. 24, 2004

(87) PCT Pub. No.: WO03/100056

PCT Pub. Date: Dec. 4, 2003

(65) Prior Publication Data

US 2006/0088918 A1   Apr. 27, 2006

(30) Foreign Application Priority Data

May 29, 2002 (JP) .............................. 2002-156049
Jan. 17, 2003 (JP) .............................. 2003-008931

(51) Int. Cl.
*C12N 9/12* (2006.01)
*C12N 1/20* (2006.01)
*C12P 19/30* (2006.01)
*C12P 21/06* (2006.01)
*C07H 21/04* (2006.01)

(52) U.S. Cl. ..................... 435/194; 435/89; 435/252.3; 435/69.1; 435/320.1; 536/23.2

(58) Field of Classification Search ................. 435/194, 435/89, 252.3, 69.1; 536/23.2
See application file for complete search history.

(56) References Cited

FOREIGN PATENT DOCUMENTS

WO  01/53513  7/2001

OTHER PUBLICATIONS

Shiba T. et al., Polyphosphate:AMP Phosphotransferase as a Polyphosphate-Dependent Nucleoside Monophosphate Kinase in Actinobacter johnsonii 210A, J. Bactriol. 2005, 187, 1859-1865.*

Database EMBL [Online] May 8, 2003, "Acinetobacter johnsonii pap gene for polyphosphate-AMP phosphotransferase, complete cds." Retrieved from EBI accession No. EM_PRO: AB092983.
Ishige, Kazuya et al., "Inorganic polyphosphate kinase and adenylate kinase participate in the polyphosphate: AMP phosphotransferase activity if *Escherichia coli*", Proceedings of the National Academy of Sciences of the United States of America, vol. 97, No. 26, Dec. 19, 2000, pp. 14168-14171.
Shiba, T. et al. "Inorganic Polyphosphate and Polyphosphate Kinase: Their Novel Biological Functions and Applications", Biochemistry (Moscow), vol. 65, No. 3, pp. 315-323.
Itoh, Hiromichi et al. "Polyphosphate Synthetic Activity of Polyphosphate:AMP Phosphotransferase in Acinetobacter johnsonii 210A", Journal of Bacteriology, vol. 186, No. 15, pp. 5178-5181.
Cornelus F. Bonting et al., Properties of Polyphosphate:AMP Phosphotransferase of Acinetobacter Strain 210A. J.Bacteriol., vol. 173, No. 20, p. 6484-6488, Oct. 1991.
Atsushi Kameda et al., A novel ATP Regeneration System Using Polyphosphate- AMP Phosphotransferase and Polyphosphate Kinase. J.Biosci.Bioeng., vol. 91, No. 6, p. 557-563, 2001.
Sol M. Resnick et al., In Vitro ATP Regeneration from Polyphosphate and AMP by Polyphosphate:AMP Phosphotransferase and Adenylate Kinase from Acinetobacter johnsii 210A. Appl.Environ.Microbiol., vol. 66, No. 5, p. 2045-2051, May 2000.

* cited by examiner

*Primary Examiner*—Rebecca Prouty
*Assistant Examiner*—Malgorzata A. Walicka
(74) *Attorney, Agent, or Firm*—Oblon, Spivak, McClelland, Maier & Neustadt, P.C.

(57) ABSTRACT

This invention relates to a novel polyphosphate: AMP phosphotransferase (PAP), a gene coding this PAP, and their use. The PAP has the following properties:

(A) action: catalyzing of the following two reactions:

$$NMP + PolyP_{(n)} \rightarrow NDP + PolyP_{(n-1)}$$

$$dNMP + PolyP_{(n)} \rightarrow dNDP + PolyP_{(n-1)}$$

(wherein NMP represents nucleoside monophosphate, NDP represents nucleoside diphosphate, dNMP represents deoxynucleoside monophosphate, dNDP represents deoxynucleoside diphosphate, n represents degree of polymerization of the polyphosphate which is an integer of up to 100);

(B) substrate specificity: specific to AMP, GMP, IMP, dAMP, and dGMP, also acting with CMP, UMP, dCMP, and TMP;

(C) molecular weight: about 55 to 56 Kd (kilodalton); and (D) specific activity: at least 70 units per 1 mg of enzyme protein.

10 Claims, 8 Drawing Sheets

Fig. 2

```
                10         20         30         40         50         60         70         80         90
GAGCTCCACCGCGGTGGCGGCCGCTCTAGAACTAGTGGATCTTTTCAGCAATTGCATTGCCACTTGTTCATCCAGTCGTCCACCGCCAAAATC
               100        110        120        130        140        150        160        170        180
GCCAACTCAACCCCAGAGGTACCGGTTTTAATGGCATTTTCAGGAATTAATTTCTCTTGTTGCCCATATTGCTCAAGCGCCAATT
               190        200        210        220        230        240        250        260        270
TGTCCTGCCAAAGCGTCAAATCTGGGCCACCATATAAACGGTTGATAAAATACTCGGCCATCAACAGAGATTTGCTTTTCGCGAAAGCT
               280        290        300        310        320        330        340        350        360
TTGTTGTGGGTACGCGTGCATTCGGCTGTCGTTTTTCCCAGACTTGCACATCTGTAAACGTTGGAAGAGCACCGAATCTTGATGATAATGCAAT
               370        380        390        400        410        420        430        440        450
TGGTAATACTGTGTTCTAAAAGCTCATCGAGGGCCGGCCAGTTTGGACATTTGCTGTCGTCCAGTTCTCTATTTAAAGATAGCTAAATCTTAGTCCG
               460        470        480        490        500        510        520        530        540
TGATGACGGAACTCGCTATGACAAAGTGACAAAAAAAAACTATTTATTTGTGGTCAGTTTGATGTAGAAGTAGTCAAAAGATACATATGAAA
               550        560        570        580        590        600        610        620        630
ATCATCTAGACCATCATTTTTAGGATCTAGTGATATGATTAAATAGAAAAAAAGGAGGGGGCCATGGATACAGAAACGATCGCCAGTGCA
                                                                      M  D  T  E  T  I  A  S  A
               640        650        660        670        680        690        700        710        720
GTGCTGAATGAAGAACAGCTTTCACTGGACTTAATTGAAGCGCAATATGCGTTGATCAATCCGTTGATCAGAGCAATGCAAAAGTTTA
 V  L  N  E  E  Q  L  S  L  D  L  I  E  A  Q  Y  A  L  M  N  T  R  D  Q  S  N  A  K  S  L
               730        740        750        760        770        780        790        800        810
GTGATTTTGGTCAGTGGAATCGAATCTGAAACTGAAAAGGCGGTAAAGGCCGGTGAAACAGCCTCCCGGATCTCCGATCCTCGTTTTTATGTC
 V  I  L  V  S  G  I  E  L  A  G  K  K  G  E  A  V  K  Q  L  R  E  W  V  D  P  R  F  L  Y  V
               820        830        840        850        860        870        880        890        900
AAAGCCGATCCACCCATCTGTTTAATCTAAAACAGCCTTTTTGGCAGCCCTACCCGATTTGTGCTGCGAAGGCAAATTATGGTG
 K  A  D  P  P  H  L  F  N  L  K  Q  P  F  W  Q  P  Y  T  R  F  V  P  A  E  G  Q  I  M  V
               910        920        930        940        950        960        970        980        990
TGGTTTGGTAATTGGTTATGGGGATTTGTTGCTACGGCATGCATGCTTCAAAGCCTTTAGATGAATGACACTTTGTTTGATGAATACGTCAGC
 W  F  G  N  W  Y  G  D  L  L  A  T  A  M  H  A  S  K  P  L  D  D  T  L  F  D  E  Y  V  S
              1000       1010       1020       1030       1040       1050       1060       1070       1080
AATATGCGGGCTTTTGAACAGGACTTGAAAAATAACAACGTAGATGTCTTAAAGTTTGGTTCGATTTGTCGTGGAAGTCTCGCAAAAG
 N  M  R  A  F  E  Q  D  L  K  N  N  N  V  D  V  L  K  V  W  F  D  L  S  W  K  S  L  Q  K
              1090       1100       1110       1120       1130       1140       1150       1160       1170
CGTCTAGATGATGATATGGACCCGAGCGAAGTGCATTGGCATAAGTTGCATGGCTAGACTGGCGCAATAAAAAACAATATGCACACCTTACAA
 R  L  D  D  M  D  P  S  E  V  H  W  H  K  L  H  G  L  D  W  R  N  K  K  Q  Y  D  T  L  Q
              1180       1190       1200       1210       1220       1230       1240       1250       1260
AAGCTACGTACGGCCTTCACCGATGACTGGCAAATCATTGATGGTGAAGATGAGGATTTGCGTAATCACAATTTTGCACAAGCAATTTTA
 K  L  R  T  R  F  T  D  D  W  Q  I  I  D  G  E  D  E  D  L  R  N  H  N  F  A  Q  A  I  L
              1270       1280       1290       1300       1310       1320       1330       1340       1350
ACGGCACTACGACACTGCCCAGAGCATGCCAAGCAGCAAGGCGCTAAAATGGCACCAATACCAGATATTCTGACTCAGTTTGAA
 T  A  L  R  H  C  P  E  H  E  K  K  A  A  L  K  W  Q  Q  A  P  I  P  D  I  L  T  Q  F  E
```

First part

Fig. 3

Second part

```
              1360        1370        1380        1390        1400        1410        1420        1430        1440
GTCCCTCAAGCTGAGGATGCGAACTATAAATCAGAATTGAAAAAACTCACCAAACAGTGGCCGATGCCATGCCTGTGATGACCGTAAA
 V  P  Q  A  E  D  A  N  Y  K  S  E  L  K  K  L  T  K  Q  V  A  D  A  M  R  C  D  D  R  K 1450        1460        1470        1480        1490        1500        1510        1520        1530
GTGGTGATTGCTTTTGAAGGTATGGATGCTGCGGGTAAAGGGGGCGATTAAGCTATTGTGAAAAAGCTCGACCACGAGAATATGAA
 V  V  I  A  F  E  G  M  D  A  A  G  K  G  G  A  I  K  R  I  V  K  K  L  D  P  R  E  Y  E 1540        1550        1560        1570        1580        1590        1600        1610        1620
ATTCATACCATTGCCGCACCTGAAAAATATGAGTTACGCCGTCCTTATCTGTGGAGCAAATTGCAGTCGGATGACATCACT
 I  H  T  I  A  A  P  E  K  Y  E  L  R  R  P  Y  L  W  R  F  W  S  K  L  Q  S  D  D  I  T 1630        1640        1650        1660        1670        1680        1690        1700        1710
ATTTTGATCGGACTGGTATGGAGCGTTTAGTCGAGCGGGTAGAAGGCTTCGAACCGAGGTAGAGTGGCAACGCCTTATGCGGAA
 I  F  D  R  T  W  Y  G  R  V  L  V  E  R  V  E  G  F  A  T  E  V  E  W  Q  R  A  Y  A  E 1720        1730        1740        1750        1760        1770        1780        1790        1800
ATCAATCGTTTGAAAAACCTCAGTAGCAGCCAAACCGTGCTGCTGATTAAGTTTTGGCTGGCAATTGATAAAGATGAACAGCAGCCGT
 I  N  R  F  E  K  N  L  S  S  S  Q  T  V  L  I  K  F  W  L  A  I  D  K  D  E  Q  A  A  R 1810        1820        1830        1840        1850        1860        1870        1880        1890
TTTAAAGCCCGCGAAAGTACTCCGCATAAACGTTTAAAATTACCGAAGAAGATTGGCGCAATGCCGACAAATGGATGACTATTAAAG
 F  K  A  R  E  S  T  P  H  K  R  F  K  I  T  E  E  D  W  R  N  R  D  K  W  D  D  Y  L  K 1900        1910        1920        1930        1940        1950        1960        1970        1980
GCAGCCGCGGGATATGTTTGCCATACCGACACCAGCTTGGTATATTTCCACCAATGATAAACAACAGGCCCGCATTGAA
 A  A  D  M  F  A  H  T  D  T  S  Y  A  P  W  Y  I  S  T  N  D  K  Q  Q  A  R  I  E 1990        2000        2010        2020        2030        2040        2050        2060        2070
GTCTTAAGGGCAATTTTAAAACAGTCTCAAAGCGGATCGCAAGCGGATCGCGACACGGATTAAAAAAATTAAAAACGGTCATTTGACCGTTTTTATA
 V  L  R  A  I  L  K  Q  L  K  A  D  R  D  T  D  *

2080        2090        2100        2110        2120        2130        2140        2150        2160
GAGGCAGATTTAGTTTTTAACTTAAGGGAATTTGGGCACTCGGCCGCTGCAACAGGAACACCTTGTTCAGCGGCTTGTTTTAGTTGAATG 2170        2180        2190        2200        2210        2220        2230        2240        2250
CCTTTGGCGAGCTTATACGACTCTTCCACATGGGTTTCCGCCAATTTTTTCATCACGACATAACCCAAGCTGGCCGCAATCATTGTCCA 2260        2270        2280        2290        2300        2310        2320        2330        2340
CCTAAGGGAATAAATTTAGTGACTTGTTTGGTAATGAATTTGGCTGCCATGTTATTGATGATTTTTCACGGCTGTACGCGACACC 2350        2360        2370        2380        2390        2400        2410        2420        2430
AGTCCAGAGAACTCCACACGTTTACCCAGTTCTGACCAATGTATTTGCTTAGTTTGCGTAGACACTGACTTGCTCAGGGGTT 2440        2450
AAACCAAAGCGGGCGTTAAC
```

POLYPHOSPHATE:AMP PHOSPHOTRANSFERASE

TECHNICAL FIELD

This invention relates to a novel polyphosphate:AMP phosphotransferase, a gene coding for this phosphotransferase, and their use.

BACKGROUND ART

Recent progress in genetic engineering has enabled large scale production of various enzymes at a low cost, and economical process using an enzymatic reaction has also been enabled for the production of physiologically active substances of value that has traditionally been produced by means of bioconversion using a live bacterium, fermentation, or chemical synthesis.

In the meanwhile, an enzymatic reaction requiring energy as in the case of phosphorylation and amination needs adenosine 5'-triphosphate (ATP) for its energy donor or phosphate donor. In the conventional microbial transformation and fermentation, ATP has been supplied by the microorganism employed, whereas, in the case of the enzymatic process, addition of ATP to the reaction system and development of efficient ATP regeneration system are required.

However, process of inexpensive ATP synthesis has not yet been established and commercially available ATP is still very expensive. In addition, both the substrate and the enzyme used in the common ATP regeneration system, namely, the combination of phosphocreatine and phosphocreatine kinase, or acetyl phosphate and acetate kinase are very expensive, and their use has been unpractical and limited to the laboratory level.

In contrast to such high price of the ATP, adenosine 5'-monophosphate (AMP) can be produced at a relatively low cost. ATP is currently produced either by chemical synthesis or by using microorganism or yeast from AMP or adenine. Accordingly, development of an efficient ATP regeneration process has been highly awaited that can be used in the enzymatic reaction system using the ATP wherein the ATP is enzymatically produced from the relatively inexpensive AMP and the consumed ATP is efficiently regenerated instead of adding the expensive ATP.

In constructing a practical ATP generation/regeneration system, selection of the phosphate donor used is also important, and polyphosphate, which is inexpensive and stable, has been considered the most promising candidate of the phosphate donor. Enzymes which are known to be involved in the metabolism of the polyphosphate and which also act with adenosine nucleotide include polyphosphate kinase and polyphosphate:AMP phosphotransferase (hereinafter abbreviated as "PAP").

PAP is an enzyme which phosphorylates AMP to produce ADP by using polyphosphate as the phosphate donor (J. Bacteriol., 173, 6484-6488(1991)). Zenhder et al. has reported that an ATP generation/regeneration system wherein AMP and polyphosphate are the substrates functions, when PAP obtained from Acinetobacter johnsonii is partially purified, and the partially purified PAP is used in combination with adenylate kinase (Appl. Environ. Microbiol., 66, 2045-2051(2000)). Kameda et al. has reported that, in the enzymatic reaction system wherein ATP is consumed to generate AMP, a system wherein ATP is generated from AMP using polyphosphate as the phosphate donor functions efficiently when the combination of the PAP from Myxococcus xanthus and E. coli polyphosphate kinase is used.

However, PAP is present in the Acinetobacter johnsonii cell in an extremely small amount, and with regard to the use of the crude PAP such as cell extract, a problem has been pointed out that contamination of the enzymes which decompose the substance involved in the reaction (AMP, ADP, ATP, reaction substrate and/or reaction product) may invite loss of reaction efficiency. Such problem can be obviated by the use of highly purified PAP instead of the crude enzyme. PAP, however, is very unstable, and the purification procedure of PAP is far too complicated to adopt such purified PAP into practical use.

In coping with such problem, the inventors of the present invention estimated that such problem can be challenged by producing the PAP of Acinetobacter johnsonii in a large amount using a recombinant DNA technique. However, the amino acid sequence of the enzyme and the gene for such enzyme have not been reported at all.

DISCLOSURE OF THE INVENTION

The inventors of the present invention have succeeded in the mass-production of the PAP in E. coli by constructing a screening system adapted for the gene cloning by PAP activity, and cloning the gene coding for the PAP by using the thus constructed screening system. In the analysis of the thus produced recombinant PAP, the inventors also found that the enzyme has an extremely high specific activity, and combination of such enzyme with adenylate kinase enables construction of an efficient ATP generation/regeneration system.

Unexpectedly, the inventors also found that the recombinant PAP has the activity of phosphate-transfer using polyphosphate for the phosphate donor to generate nucleoside diphosphate even if the nucleoside monophosphate were not AMP or GMP, and this is a difference from the conventional PAP obtained from Acinetobacter johnsonii.

While nucleoside diphosphate has been generally found useful as a starting material for enzymatically synthesizing polynucleotide used in medical or chemical commodities, its synthesis has been far from easy. In the case of bioconversion, the phosphorylation can not be terminated at the diphosphate stage, and chemical phosphorylation has been the only usable way for the nucleoside diphosphate production. However, chemical phosphorylation is associated with the problem of simultaneous occurrence of the side reaction that results in the formation of byproducts, and isolation and purification of the target nucleoside diphosphate from the reaction solution has been extremely complicated. In view of such situation, development of an efficient process for synthesizing the nucleoside diphosphate by enzymatic phosphorylation of the nucleoside monophosphate is highly awaited, and PAP has been conceived as one candidate for the enzyme used in the enzymatic synthesis.

However, Zehnder et al. has reported that, PAP from Acinetobacter johnsonii is AMP-specific, and while some phosphate-transfer is found for GMP, no phosphotransfer at all was found for other nucleotides (CMP, UMP, and IMP) (Appl. Environ. Microbiol., 66, 2045-2051 (2000)), and it has been conceived that, PAP can not be used in the synthesis of nucleoside diphosphate by enzymatic phosphorylation of the nucleoside monophosphate.

The inventors of the present invention have made an intensive study based on the novel findings as described above, and completed the present invention. This invention relates to the PAP (the PAP of the present invention) having the physical and chemical properties as described below:

(A) action: catalyzing the following two reactions:

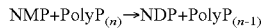

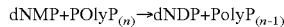

(wherein NMP represents nucleoside monophosphate, NDP represents nucleoside diphosphate, dNMP represents deoxynucleoside monophosphate, dNDP represents deoxynucleoside diphosphate, n represents degree of polymerization of the polyphosphate which is an integer of up to 100);

(B) substrate specificity: specific to AMP, GMP, IMP, dAMP, and dGMP, also acting with CMP, UMP, dCMP, and TMP;

(C) molecular weight: about 55 to 56 Kd (kilodalton); and (D) specific activity: at least 70 units per 1 mg of enzyme protein.

This invention also relates to a PAP having the amino acid sequence of SEQ ID NO: 1 or the amino acid sequence of SEQ ID NO: 1 wherein deletion, substitution, or addition of one to several amino acids has occurred.

This invention also relates to a PAP gene encoding the amino acid sequence of SEQ ID NO: 1 or the amino acid sequence of SEQ ID NO: 1 wherein deletion, substitution, or addition of one to several amino acids has occurred.

This invention also relates to a PAP gene having the nucleotide sequence of SEQ ID NO: 2 or the nucleotide sequence of SEQ ID NO: 2 wherein deletion, substitution, or addition of one to several nucleotides has occurred.

This invention also relates to a DNA fragment which hybridizes with the gene as described above under stringent conditions, and which codes for the polypeptide having PAP activity.

This invention also relates to a method for producing nucleoside diphosphate wherein the nucleoside diphosphate is enzymatically produced from nucleoside monophosphate by using the PAP of the present invention as the enzyme and polyphosphate as a phosphate donor.

This invention also relates to a method for producing ATP wherein ATP is enzymatically produced from AMP by using two enzymes, namely, the PAP of the present invention and adenylate kinase as the enzyme and polyphosphate as a phosphate donor.

This invention also relates to an ATP generation/regeneration system comprising AMP, polyphosphate, PAP, and adenylate kinase wherein the PAP used is the PAP of the present invention.

Finally, this invention also relates to a method for producing a compound by using an ATP-consuming enzymatic reaction, wherein ATP is regenerated from the AMP simultaneously with the enzymatic reaction by using an ATP regeneration system comprising polyphosphate, PAP, and adenylate kinase, and wherein the PAP used is the PAP of the present invention.

BRIEF DESCRIPTION OF THE DRAWINGS

FIG. 2 shows the first half of the nucleotide sequence of the 2.5 kb DNA fragment including the PAP gene, and the first half of the amino acid sequence of the PAP.

FIG. 3 shows the second half of the nucleotide sequence of the 2.5 kb DNA fragment including the PAP gene, and the second half of the amino acid sequence of the PAP.

Figure 1:
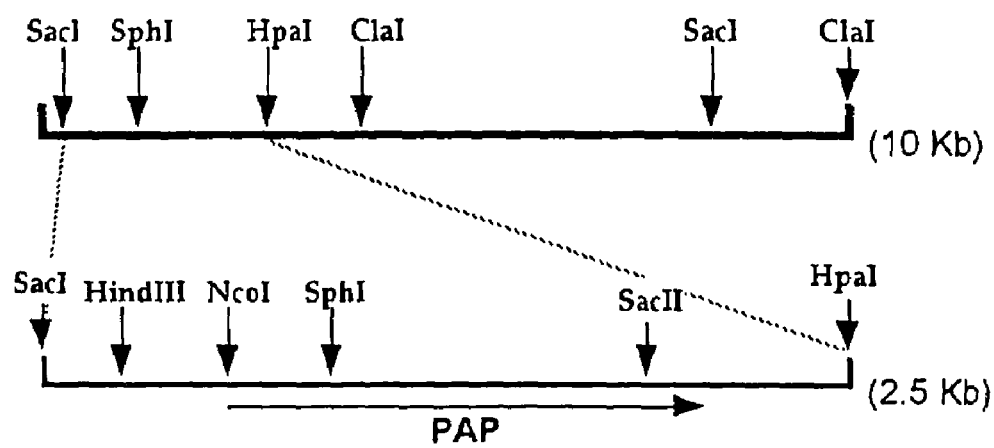
FIG. 1 is a restriction map of the DNA fragment of about 10 kb including the PAP gene obtained from *Acinetobacter johnsonii* strain 210A. The PAP gene is included in SacI-HpaI DNA fragment.

BEST MODE FOR CARRYING OUT THE INVENTION (1) PAP of the Present Invention

The PAP of the present invention has the physical and chemical properties as described below. (Also, see the Examples as will be presented later.)

(A) Action: PAP catalyzes the following two reactions:

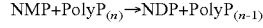

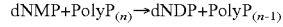

(wherein NMP represents nucleoside monophosphate, NDP represents nucleoside diphosphate, dNMP represents deoxynucleoside monophosphate, dNDP represents deoxynucleoside diphosphate, n represents degree of polymerization of the polyphosphate which is an integer of up to 100).

(B) Substrate specificity: PAP acts specifically to AMP, GMP, IMP, DAMP, and dGMP, and it also acts with CMP, UMP, dCMP, and TMP.

(C) Molecular weight: PAP has a molecular weight of about 55 to 56 Kd (kilodalton).

(D) Specific activity: PAP has a specific activity of at least 70 units per 1 mg of enzyme protein.

(E) Optimal pH: around pH 8.5.

(F) Optimal temperature: around 50° C.

(G) pH stability: around pH 7 to 9.

(H) Thermal stability: PAP is stable up to about 50° C.

The "unit" used herein is the unit measured under the following conditions, and 1 unit corresponds to the activity of producing 1 μmole of ADP at 37° C. in 1 minute.

<Measurement Conditions>

Sample enzyme is added to 50 mM Tris HCl buffer solution (pH 7.8) containing 20 mM magnesium chloride, 10 mM AMP, and polyphosphate (30 mM calculated in terms of inorganic phosphate) and the reaction is allowed to proceed by incubating the temperature at 37° C., and the reaction is thereafter terminated by a heat treatment at 100° C. for 1 minute, and amount of ADP in the reaction solution is measured by high performance liquid chromatography (HPLC).

The PAP of the present invention has the amino acid sequence represented by SEQ ID NO: 1, and in particular, the recombinant PAP produced by recombinant DNA process is substantially pure in terms of enzymatic activity, and such recombinant PAP is free from the AMP-degrading activity which is disadvantageous for phosphorylation of the AMP.

The amino acid sequence may also be the one wherein deletion, substitution, modification, or addition of one to several amino acids has occurred as long as the activity of catalyzing the reactions as described above is retained. The deletion, substitution, modification, or addition of the amino acid sequence may be induced by site specific mutagenesis (for example, Proc. Natl. Acad. Sci. USA, 81, 4662-5666 (1984); Nucleic Acid Res. 10, 6487-6500(1982); Nature 316, 601-605(1985)) or the like which were known in the art before the filing of the present invention. The PAP of the present invention also includes an enzyme which has a homology of at least 90%, and more preferably at least 95% with the amino acid sequence of SEQ ID NO: 1 as long as the activity of catalyzing the reactions as described above is retained.

The PAP of the present invention is prepared by cloning the gene coding for the enzyme having the amino acid sequence shown in SEQ ID NO: 1, typically, the PAP gene having the nucleotide sequence shown in SEQ ID NO: 2 from *Acinetobacter johnsonii*, and using this gene. When explained by referring to an exemplary case of the gene from *Acinetobacter johnsonii*, FIGS. 2 and 3 show the sequencing result of the nucleotide sequence of the DNA fragment cleaved by SacI and HpaI in the restriction map of FIG. 1, and the sequence of nucleotide numbers 604 to 2031 in FIGS. 2 and 3 corresponds to the structural gene of PAP, and this sequence is the same as the nucleotide sequence shown in SEQ ID NO: 2.

In the present invention, a gene having the nucleotide sequence of SEQ ID NO: 2 wherein deletion, substitution, insertion, or addition of one or plural nucleotides has occurred in such sequence; a gene which hybridizes with such gene under stringent conditions; and a gene which has a homology of at least 90%, and more preferably at least 95% with the nucleotide sequence shown in SEQ ID NO: 2 may also be employed as long as the gene is capable of producing the PAP of the present invention.

As in the case of the amino acid sequence as described above, the gene wherein deletion, substitution, insertion, or addition of single or plural nucleotides has occurred means the gene wherein nucleotides of the number that can be deleted, substituted, inserted, or added by the technique known in the art such as site specific mutagenesis has been deleted, substituted, inserted, or added. The hybridization under stringent conditions means the hybridization using a solution containing 5×SSC (1×SSC corresponds to 8.76 g of sodium chloride and 4.41 g of sodium citrate dissolved in 1 liter of water), 0.1% w/v N-lauroylsalcosine sodium salt, 0.02% w/v SDS, and 0.5% w/v blocking agent, under the reaction temperature conditions of about 60° C. for about 20 hours.

In the present invention, use of a gene further comprising SD sequence (Shine-Dalgarno Sequence) in the upstream the gene coding for the PAP is also favorable, since the yield of the enzyme can be markedly improved by the use of such gene.

Cloning of such gene, preparation of the expression vector using the thus cloned DNA fragment, preparation of the PAP using such expression vector, and the like are well known to those skilled in the field of molecular biology, and such process may be done, for example, by using the procedure described in "Molecular Cloning" (Maniatis et al. ed., Cold Spring Harbor Laboratories, Cold Spring Harbor, N.Y. (1982)).

In an exemplary method, amino acid sequence on N-terminal, C-terminal, or the like of the PAP purified from a microorganism belonging to genus *Acinetobacter* may be partly sequenced by a known method, and the oligonucleotide corresponding to the thus determined sequence is synthesized. Then, the DNA fragment containing the gene coding for the PAP may be cloned from the chromosomal DNA of the bacterium belonging to genus *Acinetobacter* by using the thus synthesized oligonucleotide as the probe. Alternatively, chromosomal DNA may be cleaved by using appropriate restriction enzymes, and a genomic library may be produced by the method commonly used in the art. The resulting genomic library may be screened based on the PAP activity to thereby clone the target gene.

There is, however, a fair risk that the PAP is inactivated when the PAP is purified to a high degree, and therefore, use of a screening system using the PAP activity is preferable. The PAP activity used in the screening is preferably the activity of generating ATP from AMP by the combination of the PAP with polyphosphate kinase (PPK). More specifically, PAP and PPK may be used for generation of the ATP using AMP for the substrate and isotope-labeled polyphosphate for the phosphate donor to thereby detect the generation of the isotope-labeled ATP.

The host used for the cloning is not particularly limited. Use of *E. coli*, however, is preferable in view of the working and handling convenience.

Expression system with high expression rate of the cloned gene may be constructed by preparing a recombinant expression vector wherein expression regulatory signals (transcription initiation signal and translation initiation signal) are ligated in the upstream of the gene, after identification of the coding region of the gene through the method to sequence the nucleotide sequence of the cloned DNA fragment, for example, Maxam-Gilbert (Methods in Enzymology, 65, 499(1980)), dideoxy chain terminator method (Methods in Enzymology, 101, 20(1983)), or the like.

In order to produce the PAP in a large amount in the heterologous microorganism, the expression regulatory signals used are desirable transcription and translation initiation signals which can be regulated by an artificial means, and which are strong signals enabling a dramatic increase in the PAP yield. Examples of transcription initiation signal which can be used when the host is *E. coli* include lac promoter, trp promoter, and tac promoter (Proc. Natl. Acad. Sci. USA., 80, 21(1983), and Gene, 20, 231(1982)), and trc promoter (J. Biol. Chem., 260, 3539(1985)).

Exemplary vectors which can be used include plasmid vector, phage vector, and other vectors, and use of a plasmid vector is desirable since it can be amplified in the microorganism, it includes an adequate drug-resistant marker and cleavage site for the predetermined restriction enzymes, and it is copied in a large number in the microorganism. Examples of the plasmid vectors which can be used when the host is *E. coli* include pBR322 (Gene, 2, 95(1975)), pUC18, and pUC19 (Gene, 33, 103(1985)).

The microorganism is transformed by using the thus produced recombinant vector. The microorganism used for the host is not particularly limited as long as it has high safety and handling convenience, and *E. coli*, yeast, and other microorganisms commonly used in the DNA recombinant techniques can be used as desired. Use of *E. coli*, however, is favorable, and exemplary strains include K12, C600, JM105, JM109 (Gene, 33, 103-119(1985)), and other strains normally used in the DNA recombinant experiments.

Various methods have been reported for use in the transformation of a microorganism, and an adequate method may be selected depending on the type of the microorganism used for the host. When *E. coli* is used for the host, *E. coli* may be transformed by the treatment with calcium chloride followed by the introduction of the plasmid to the interior of the cell at low temperature (J. Mol. Biol., 53, 159 (1970)).

The resulting transformant is cultivated in a culture medium wherein the microorganism is propagatable, and the cultivation is continued and the expression of the cloned PAP gene is induced until a large amount of the PAP is accumulated in the microorganism. The transformant may be cultivated by a method commonly used in the art using a culture medium containing a carbon source, a nitrogen source, and other nutrient sources necessary for the propagation of the microorganism cultivated. For example, when E. coli is used for the host, the culture medium used may be those commonly used for the cultivation of E. coli such as 2xYT medium (Methods in Enzymology, 100, 20 (1983)), LB medium, M9CA medium (Molecular Cloning, supra), and the cultivation may be conducted at an incubation temperature of 20 to 40° C. with aeration shaking. When a plasmid is used for the vector, an appropriate antibiotic agent (ampicillin, kanamycin, or the like corresponding to the drug-resistant marker) of an appropriate amount is added to the culture medium to thereby prevent loss of the plasmid in the course of the cultivation.

When the expression of the PAP gene should be induced during the cultivation, the gene expression may be induced by the method commonly used with the promoter used. For example, when the promoter used is lac promoter or tac promoter, an expression inducing agent such as isopropyl-β-D-thiogalactopyranoside (hereinafter abbreviated to as IPTG) may be added at an appropriate amount in the intermediate period of the cultivation.

The cells are collected from the thus produced culture by membrane separation, centrifugation, or the like. While the collected cells may be used as PAP with no further treatment, the PAP used is preferably a cell-free extract prepared by suspending the cells collected in an appropriate buffer solution, lyzing the cell by a physical treatment using ultrasonication, French press, or the like, or by an enzymatic treatment using lysozyme or the like, and removing the bacterial residue to obtain the extract. While cell-free extract may be used for the enzyme source with no further treatment since the cell-free extract contains an abundant amount of PAP, the PAP used may also be a partially purified product or a purified product prepared by either one or combination of two or more of heat treatment, ammonium sulfate precipitation, dialysis, treatment using a solvent such as ethanol, various chromatographic treatments, and other treatments commonly used in the enzyme purification.

(2) Use of PAP in the Present Invention

The thus prepared PAP of the present invention can be used in the synthesis of nucleoside diphosphate or deoxynucleoside diphosphate, and in the synthesis or regeneration of the ATP.

First, the nucleoside 5'-monophosphate (NMP) or the deoxynucleoside 5'-monophosphate (dNMP) used in the synthesis of nucleoside 5'-diphosphate (NDP) or deoxynucleoside 5'-diphosphate (dNDP) may be a commercially available product, and it may be used at a concentration in the range of, for example, 1 to 200 mM, and preferably 10 to 100 mM.

The polyphosphate used may also be a commercially available product, and it may be used at a concentration in the range of 1 to 1000 mM, and preferably 10 to 200 mM calculated in terms of inorganic phosphate. The degree of polymerization (n) of the polyphosphate may be up to 100, and preferably about 10 to 50.

The synthesis of the NDP or dNDP may be accomplished by the reaction wherein NMP or dNDP and polyphosphate are added to a buffer solution at a pH in the range of 4 to 9, and at least 0.001 unit/ml, and preferably 0.001 to 10 units/ml of the PAP of the present invention is added to the solution at 20° C. or higher, and preferably at 30 to 40° C. for about 1 to 50 hours with optional stirring.

The thus produced NDP or dNDP may be isolated and purified by a chromatographic process or other process known in the art.

The ATP synthesis may be accomplished by converting AMP to ADP, and then, to ATP by using the PAP of the present invention and adenylate kinase in the presence of polyphosphate.

The AMP added to the reaction solution may be a commercially available product, and it may be used at an adequate concentration selected from the range of, for example, 1 to 200 mM, and preferably 10 to 100 mM.

The polyphosphate added may also be a commercially available product, and it may be used at a concentration selected from the range of 1 to 1000 mM, and preferably 10 to 200 mM calculated in terms of inorganic phosphate. The degree of polymerization (n) of the polyphosphate may be up to 100, and preferably about 10 to 50.

The synthesis of the ATP may be accomplished by adding AMP and polyphosphate in an appropriate buffer solution at pH in the range of 4 to 9, and further adding at least 0.001 unit/ml, and preferably 0.001 to 10 units/ml of the PAP of the present invention and at least 0.01 unit/ml, and preferably 0.01 to 100 units/ml or more of adenylate kinase to allow the reaction to proceed at 20° C. or higher, and preferably at 30 to 40° C. for about 1 to 50 hours with optional stirring.

The thus generated ATP may be isolated and purified by a chromatographic method or other method known in the art.

The unit of the adenylate kinase activity is the one measured and calculated by the procedure as described below. Sample enzyme is added the 50 mM Tris HCl buffer solution (pH 7.8) containing 10 mM magnesium chloride, 10 mM AMP, and 10 mM ATP, and the solution is incubated at 37° C. to promote the reaction, and the reaction is terminated by a 1 minute heating at 100° C. Amount of the ADP in the reaction solution is measured by using HPLC, and the activity of producing 2 µmole of ADP at 37° C. in 1 minute is designated 1 unit.

The ATP regeneration/regeneration system comprising the AMP, the polyphosphate, the PAP of the present invention, and the adenylate kinase may be used in detecting a minute amount of ATP in the course of detecting invisible microorganisms to check the cleanliness of the food in the food plant, or in the detection of adenine nucleotide by bioluminescence, which is applicable in the measurement of freshness of meat, fish, vegetable, and other foods (see, for example, WO01/53513).

The ATP regeneration system comprising polyphosphate, the PAP of the present invention, and adenylate kinase is also applicable to the production of a compound using an ATP-consuming enzymatic reaction for allowing the ATP regeneration from the AMP to take place simultaneously with the enzymatic synthesis of the target compound thereby improving the efficiency of the synthesis.

Exemplary non-limited enzymatic reactions which can be combined with such ATP regeneration system include galactose-1-phosphate synthesis system using galactokinase, UDP synthesis system using UMP kinase, and phosphocholine synthesis system using choline kinase, and the ATP regeneration system may be applied to any ATP-consuming enzymatic reaction.

The reaction conditions of the ATP synthesis system and the enzymatic reaction may be adequately determined by conducting tests in smaller scale, and the isolation and the purification of the target compound may be accomplished by a method known in the art.

EXAMPLES

Next, the present invention is described in further detail by referring to the Examples, which by no means limit the scope of the invention. In the Examples, preparation of the DNA, cleavage with the restriction enzyme, DNA ligation by using T4 DNA ligase, and transformation with the DNA were all conducted in accordance with "Molecular cloning II" (Sambrook et al. ed., Cold spring Harbor Laboratory, Cold Spring Harbor, N.Y. (1989)). The restriction enzyme, AmpliTaq DNA polymerase, T4 DNA ligase, and other DNA related enzymes were all obtained from Takara Shuzo K. K. Quantitative measurement of the nucleotides were conducted by HPLC, and more specifically, ODS-AQ312 column manufactured by YMC was used for separation purpose with the eluent of 0.5M monopotassium phosphate solution.

Example 1

Preparation of the PAP of the Present Invention (1) Cloning of the PAP gene of *Acinetobacter johnsonii* Strain 210

(1-1) *E. coli* Polyphosphate Kinase and Isotope-labeled Polyphosphate

*E. coli* polyphosphate kinase was prepared by the method described in the document (J. Biol. Chem., 268, 633-639 (1993)). Isotope-labeled polyphosphate was prepared using the thus prepared *E. coli* polyphosphate kinase according to the method of Akiyama et al. (J. Biosci. Bioeng., 91, 557-563(2001)).

(1-2) Production of Genomic Library of *Acinetobacter johnsonii* and its Screening

*Acinetobacter johnsonii* strain 210A was inoculated in LB medium, and the cultivated overnight at 30° C. with stirring. The cells were collected by centrifugation, and chromosomal DNA was purified. The chromosomal DNA of *Acinetobacter johnsonii* was partially decomposed with restriction enzyme Sau3AI, and the fragments were fractionated by sucrose density gradient centrifugation to recover the fraction of about 7 to 10 Kb. This DNA fragment and the plasmid vector pBlueScript SK(+) (purchased from Toyobo) which had been cleaved with BamHI were ligated by using T4 DNA ligase, and *E. coli* strain JM109 (purchased from Takara Shuzo) was transformed with the solution of this DNA. The thus produced 6000 ampicillin-resistant transformants were divided into groups of 50 transformants.

After cultivating each group overnight at 37° C. in LB medium, the cells were collected by centrifugation and washed with 20 mM Tris-HCl (pH 8.0), and again suspended in the same buffer solution. BugBuster (purchased from Takara Shuzo) was added to the cell suspension at the equal amount, and the suspension was allowed to stand at room temperature for 30 minutes for cell lysis. Three volumes of 20 mM Tris-HCl (pH 8.0) was then added to prepare the cell extract.

To 20 μl of the activity detecting solution (50 mM Tris HCl (pH 8.0), 40 mM $(NH_4)_2SO_4$, 4 mM $MgCl_2$, and 1 mM AMP) containing the isotope-labeled polyphosphate (0.24 mM calculated in terms of phosphate) prepared above was added 1 μl of the cell extract, and the reaction was allowed to proceed at 37° C. for 1 hour. The reaction solution was then subjected to thin layer chromatography (using developer: 0.75M $KH_2PO_4$, pH 3.5), and the ADP formation was detected on phospho-image analyzer BASS2000 (manufactured by Fujix) for screening of the transformants. PAP activity was detected for 1 clone in the 6000 strains.

Plasmid pPAP2 having the PAP gene of *Acinetobacter johnsonii* strain 210A inserted therein was obtained from the resulting clone (FIG. 1). It is to be noted that the plasmid pPAP2 had inserted therein the chromosomal DNA of *Acinetobacter johnsonii* strain 210A which is about 10 kb, and it was internationally deposited on the basis of Budapest treaty on May 22, 2002 with the designation of plasmid DNA (pPAP2) to The National Institute of Advanced Industrial Science and Technology (an Independent Administrative Institution), International Patent Organism Depositary (Chuo-6, 1, Higashi 1-chome, Tsukuba-shi, Ibaraki, Japan (Post code, 305-8566)) with the accession number of FERM BP-8047.

(1-3) Analysis of PAP Gene of *Acinetobacter johnsonii* Strain 210

The DNA of *Acinetobacter johnsonii* strain 210A of 10 kb inserted in the pPAP2 was subcloned in various plasmids to determine the PAP activity of these transformants as described above, and it was then found that the PAP gene is located in SacI-HpaI DNA fragment of about 2.5 kb (FIG. 1). The nucleotide sequence of this DNA fragment was determined by dideoxy chain terminator method (Science, 214, 1295(1981)), and it was then found that the PAP gene codes for the polypeptide (molecular weight: 55.8 kd) comprising 475 amino acids (FIGS. 2 and 3).

(2) Preparation of *Acinetobacter johnsonii* PAP

The *E. coli* JM109 carrying the plasmid pPAP2 was cultivated overnight at 28° C. in 2xYT medium containing ampicillin at 100 μg/ml. The cells were collected by centrifugation, and suspended in the buffer solution comprising 50 mM Tris HCl (pH 7.8) and 1 mM EDTA. After ultrasonication, cell extract was collected by centrifugation. In the measurement of the extract for the PAP activity, it was found that PAP was produced at a rate of 18.1 unit per 1 ml of the culture solution, and that the activity was about 9000 folds higher than that of the contrast (the *E. coli* JM109 carrying no the plasmid).

It is to be noted that this productivity corresponds to about 150 times the productivity of the *Acinetobacter Johnsonii*. PAP was partially purified by fractionating the extract by ion exchange chromatography using DEAE TOYOPEARL 650M (TOSO) (eluent: 50 mM Tris HCl (pH 7.8), concentration gradient of 0 to 0.5M NaCl), and the collected fraction was used for the enzyme sample. The specific activity of the PAP in the collected fraction was 80.5 units/mg protein.

(3) Analysis of Various Properties of PAP (3-1) Synthesis of Various NDP (Analysis of Substrate Specificity)

To 50 mM Tris HCl buffer solution (pH 8.0) containing 100 mM $MgCl_2$, polyphosphate (10 mM calculated in terms of inorganic phosphate), and 5 mM of various NMP or dNMP was added PAP at various concentration, and the solution was incubate at 37° C. for 10 minutes. The reaction was terminated by heat treatment at 100° C. for 1 minute, and the solution after the reaction was subjected to HPLC to measure the amount of the NDP or the dNDP produced. The specific activity of each NMP or dNMP is shown in Table 1 as a relative value in relation to the specific activity of the PAP in the phosphorylation of the AMP, which is assumed 100%.

TABLE 1

| Substrate | Specific activity (relative value) |
|---|---|
| AMP | 100% |
| GMP | 10 |
| CMP | 0.09 |
| UMP | 0.13 |
| IMP | 2.2 |
| dAMP | 18 |
| dGMP | 2.6 |
| dCMP | 0.008 |
| TMP | 0.012 |

(3-2) pH Stability

PAP was incubated in either 50 mM maleate or 50 mM Tris HCl buffer solution of various pH at 37° C. for 10 minutes in the presence of 100 mM magnesium chloride to measure the residual activity. The residual activity was measured by allowing the reaction to take place at 37° C. for 10 minutes in the presence of 50 mM Tris buffer solution (pH 8.0), 100 mM magnesium chloride, 5 mM AMP, and polyphosphate (10 mM calculated in terms of inorganic phosphate), and measuring the resulting ADP by HPLC.

Figure 4:
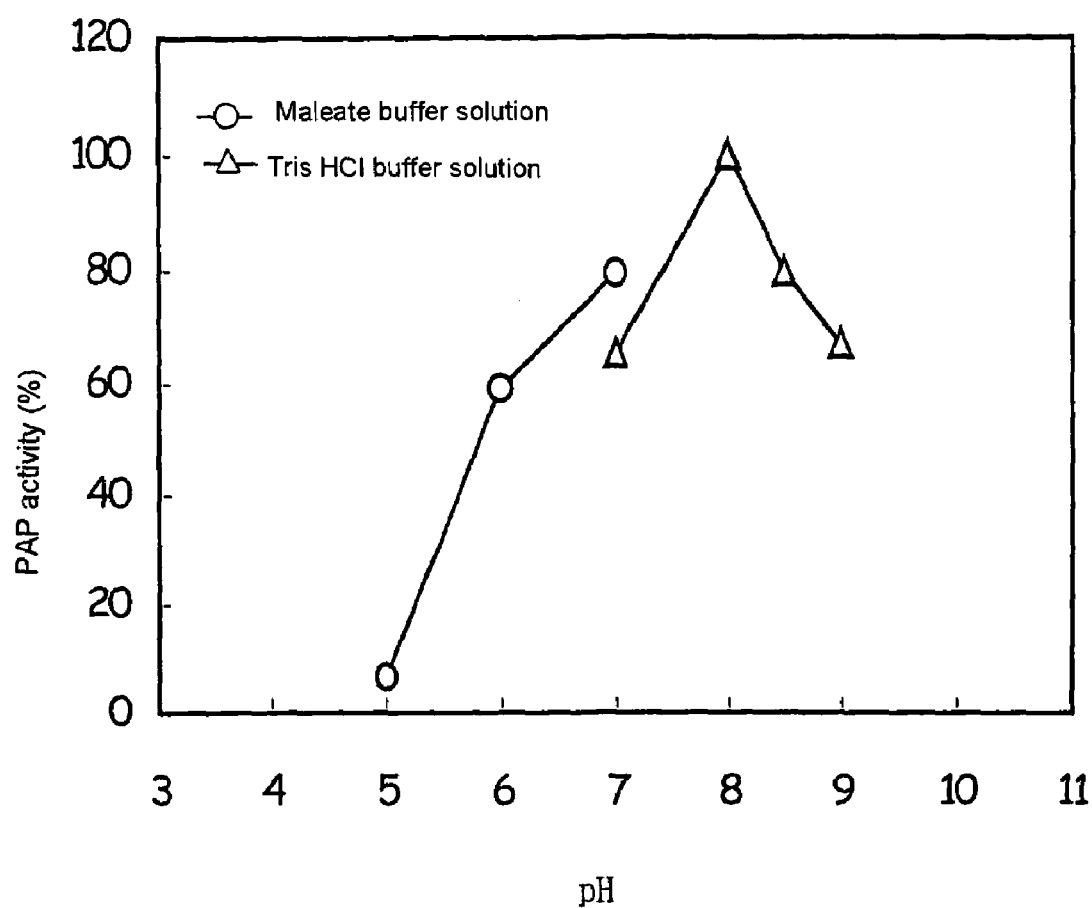
FIG. 4 shows the results of the pH stability evaluation according to the PAP of the present invention.
Figure 5:
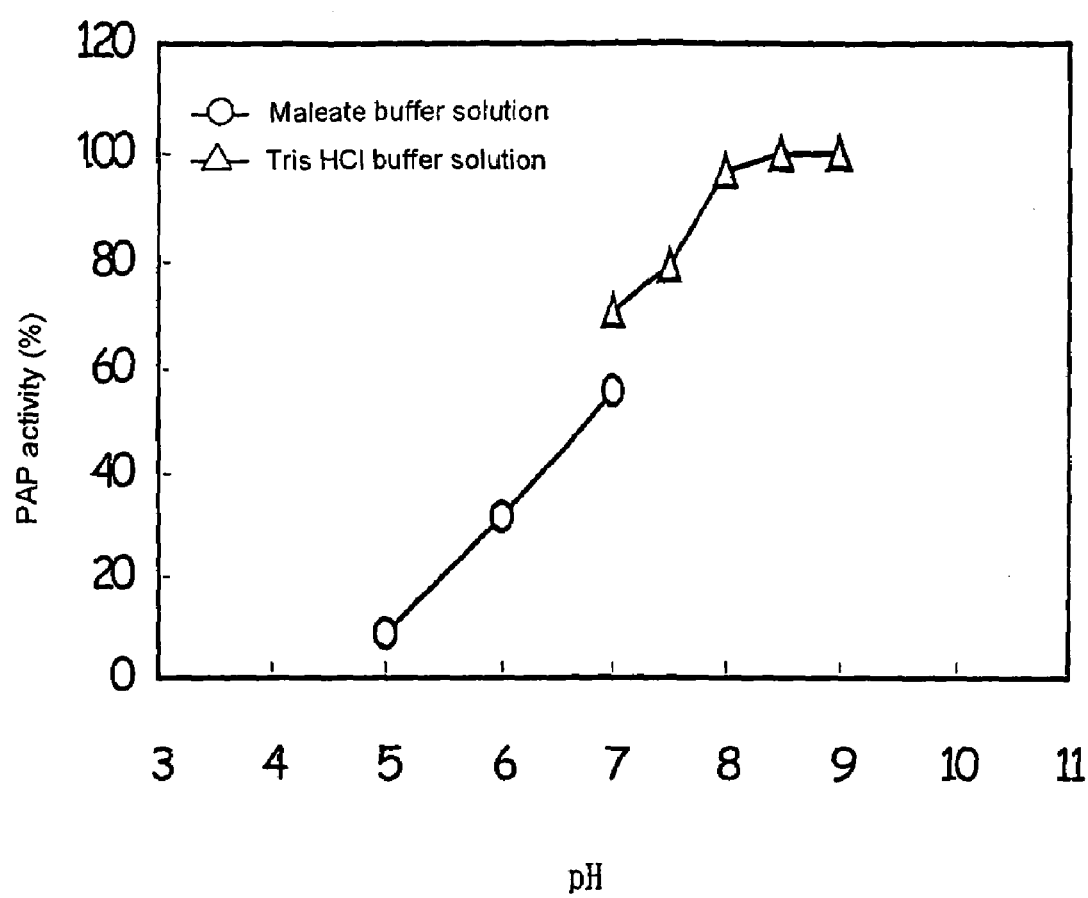
FIG. 5 shows the results of the optimal pH evaluation according to the PAP of the present invention.

As shown in FIG. 4, the enzyme of the present invention was found to exhibit an enzymatic activity of 80% or more at a pH in the range of 7 to 9 when the enzymatic activity at pH 8 was 100%.

(3-3) Optimal pH

The reaction was allowed to proceed in either 50 mM maleate or 50 mM Tris HCl buffer solution of various pH at 37° C. for 10 minutes in the presence of 100 mM magnesium chloride, polyphosphate (10 mM calculated in terms of inorganic phosphate), and 5 mM AMP to measure the amount of the ADP produced by HPLC.

As shown in FIG. 4, the optimal pH of the enzyme of the present invention was approximately 8.5.

(3-4) Thermal Stability

PAP was incubated for 10 minutes in 50 mM Tris HCl buffer solution (pH 8.0) containing 100 mM magnesium chloride in the presence or absence of polyphosphate (10 mM calculated in terms of inorganic phosphate) in the bath at various temperatures to measure the residual activity by the procedure as described above.

Figure 6:
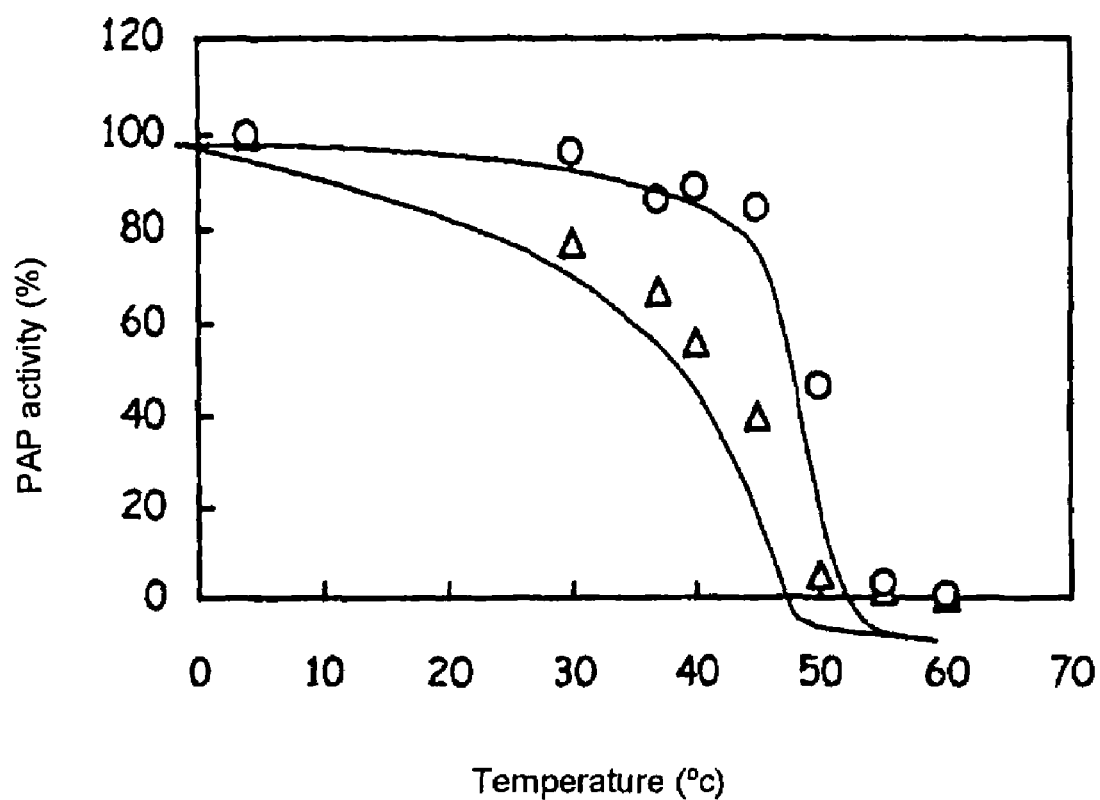
FIG. 6 shows the results of the thermal stability evaluation according to the PAP of the present invention.

As shown in FIG. 6, the enzyme of the present invention was found to be stable up to approximately 50° C. in the presence of the polyphosphate.

(3-5) Optimal Temperature

PAP was incubated for 10 minutes in 50 mM Tris HCl buffer solution (pH 8.0) containing 100 mM magnesium chloride in the presence of polyphosphate (10 mM calculated in terms of inorganic phosphate) and 5 mM AMP in the bath at various temperatures, and the enzymatic activity was evaluated by measuring the amount of ADP produced by HPLC.

Figure 7:
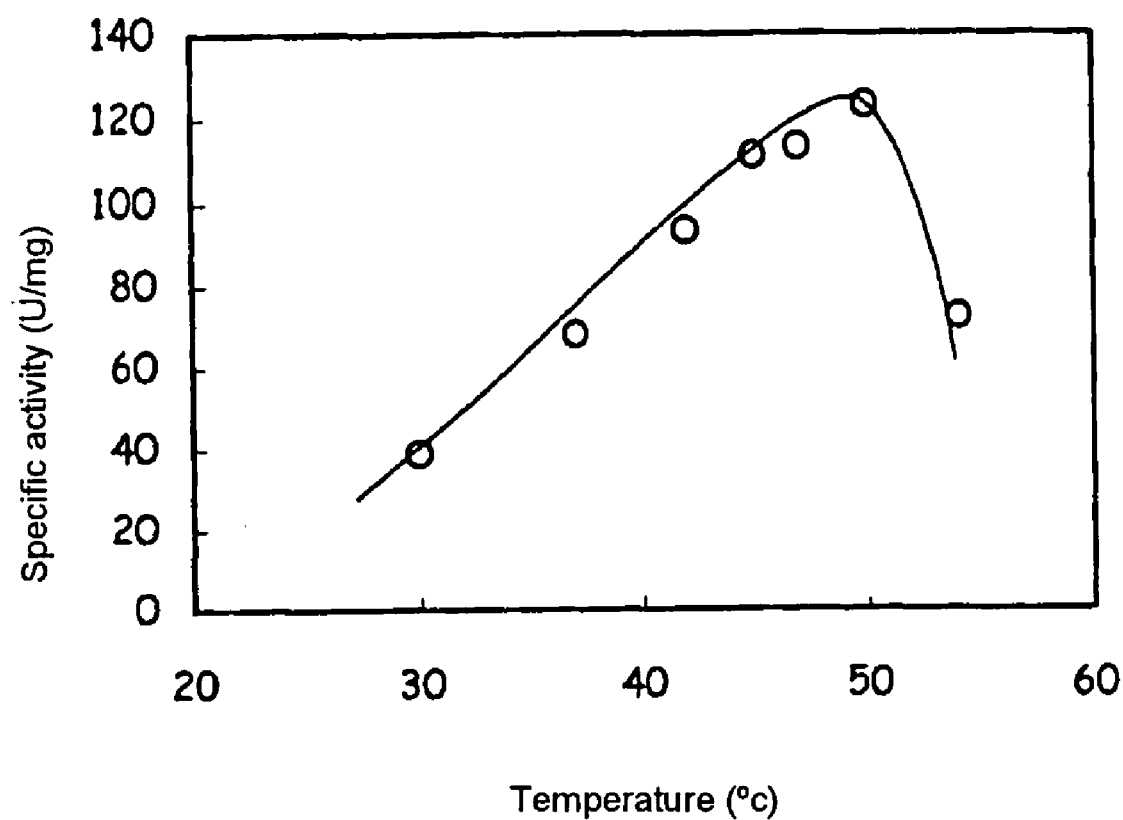
FIG. 7 shows the results of the optimal temperature evaluation according to the PAP of the present invention.

As shown in FIG. 7, optimal reaction temperature of the enzyme of the present invention was found to be approximately 50° C.

Example 2

Synthesis of ATP Using PAP and Adenylate Kinase (1) Preparation of *E. coli* Adenylate Kinase

*E. coli* adenylate kinase was prepared by the procedure described in the document (Proc. Natl. Acad. Sci. USA, 97, 14168-14171 (2000)). However, the cell extract produced by ultrasonication was used for the enzyme solution, and the specific activity of the adenylate kinase in the enzyme solution was 12.5 units/mg protein.

(2) Synthesis of ATP

To 50 mM Tris HCl buffer solution (pH 7.8) containing 20 mM $MgCl_2$, polyphosphate (30 mM calculated in terms of inorganic phosphate), and 10 mM AMP were added 1.5 units/ml of PAP and 0.4 unit/ml of adenylate kinase, and the solution was incubated at 37° C. for 60 minutes. After the completion of the reaction, amount of the nucleotide in the reaction solution was measured by HPLC.

Figure 8:
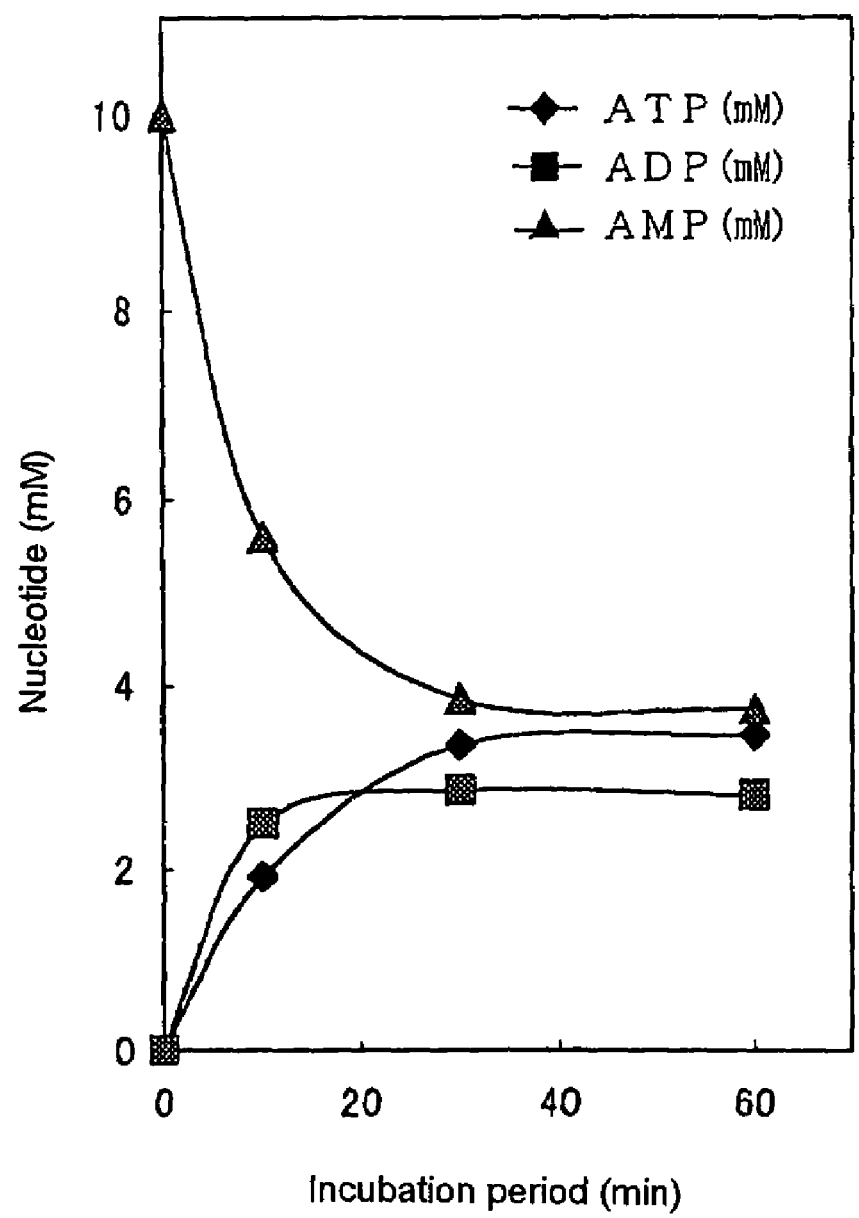
FIG. 8 shows synthesis of ADP and ATP from AMP using polyphosphate for the phosphate donor and using the PAP and adenylate kinase.

As shown in FIG. 8, it was confirmed that AMP is promptly phosphorylated by the PAP to produce ADP, and the thus produced ADP is promptly converted to ATP and AMP by the adenylate kinase that is also present in the system, the repetition of this cycle resulting in the ATP accumulation.

Example 3

Synthesis of Galactose-1-phosphate Using ATP Regeneration System Comprising the combination of PAP and Adenylate Kinase (1) Preparation of *E. coli* Galactokinase

*E. coli* strain JM109 having the plasmid pDR540 containing *E. coli* galactokinase gene (Gene, 20, 231(1982), obtained from Pharmacia) was inoculated in 2xYT medium containing 100 μg/ml ampicillin, and the *E. coli* was cultivated at 37° C. with shaking. When the cell density reached $4 \times 10^8$/ml, IPTG was added to the culture medium to a final concentration of 1 mM, and the incubation was continued at 30° C. for another 5 hours. After completion of the cultivation, the cells were collected by centrifugation and suspended in 30 ml buffer solution (50 mM Tris HCl (pH 7.8), 1 mM EDTA). The cells were lyzed by ultrasonication, and bacterial residue was removed by further centrifugation. The solution collected was subjected to ion exchange chromatography using DEAE Toyopearl 650M (Toso) (eluent: 50 mM Tris HCl (pH 7.8), concentration gradient of 0 to 0.5M NaCl) for fractionation and partial purification of the galactokinase. The thus recovered fraction was used for the enzyme solution of galactokinase. The specific activity of the galactokinase in the enzyme solution was 6.5 units/mg protein.

The unit of the glactokinase activity was the one measured and calculated by the procedure as described below. Sample enzyme was added the 100 mM Tris HCl buffer solution (pH 7.8) containing 5 mM $MgCl_2$, 10 mM ATP, and 10 mM galactose, and the solution was incubated at 37° C. to promote the reaction, and the reaction was terminated by a 1 minute heat treatment at 100° C. Amount of the galactose-1-phosphate in the reaction solution was measured by using a sugar analyzer (Dionex), and the activity of producing 1 μmole of galactose-1-phosphate at 37° C. in 1 minute was designated 1 unit.

(2) Synthesis of Galactose-1-phosphate

To 50 mM Tris HCl buffer solution (pH 7.8) containing 20 mM MgCl$_2$, polyphosphate (30 mM calculated in terms of inorganic phosphate), 5 mM AMP, and 50 mM (d) galactose were added 0.2 unit/ml PAP and 0.2 unit/ml adenylate kinase, and then, galactokinase to 0.5 unit/ml, and the solution was incubated at 37° C. for 8 hours. During the reaction, polyphosphate was also added respectively at 2 hours and 4 hours after the start of the reaction to 20 nM calculated in terms of inorganic phosphate. The reaction solution was analyzed with a sugar analyzer (Dionex), and production of 37.8 mM galactose-1-phosphate was confirmed.

Example 4

Synthesis of Nucleotide Diphosphate (1) Synthesis of Various NDP

To 50 mM Tris HCl buffer solution containing 100 mM MgCl$_2$, polyphosphate (30 mM calculated in terms of inorganic phosphate), and 10 mM of an NMP (AMP, GMP, CMP, UMP, or IMP) was added PAP at 16 units/ml, and the solution was incubated at 37° C. for 30 minutes. The results of the HPLC analysis of the reaction solution are shown in Table 2. It is to be noted that no NDP generation was found when cell extract of *E. coli* JM109 was used for the contrast.

TABLE 2

| Substrate | NDP generated |
|---|---|
| AMP | 6.76 mM ADP |
| GMP | 7.16 mM GDP |
| CMP | 0.98 mM CDP |
| UMP | 0.85 mM UDP |
| IMP | 6.75 mM IDP |

(2) Enzymatic Synthesis of IDP

To 50 mM Tris HCl buffer solution containing 100 mM MgCl$_2$, polyphosphate (65 mM calculated in terms of inorganic phosphate), and 40 mM IMP was added PAP at 16 units/ml, and the solution was incubated at 37° C. for 19 hours. The reaction solution was analyzed by HPLC, and formation of 21. 2 mM IDP was confirmed.

INDUSTRIAL APPLICABILITY

This invention provides a novel PAP and its gene. This invention has also enabled a large scale production of the PAP with no difficulty, which could not have been done by the conventional technology. An efficient synthesis and regeneration of ATP from AMP at a low cost has been realized, and combination of this with an ATP-consuming enzymatic reaction system enables regeneration of the ATP consumed in the reaction system to facilitate efficient synthesis of the target compound.

In contrast to the conventional PAP, the PAP of the present invention exhibits phosphorylation activity for various types of nucleoside 5'-monophosphate other than AMP and deoxynucleoside 5'-monophosphate, and this enables smooth production of various types of nucleoside 5'-diphosphate and deoxynucleoside 5'-diphosphate by an enzymatic process.

The invention claimed is:

1. An isolated polynucleotide, comprising SEQ ID NO:2.
2. An isolated polynucleotide, comprising a nucleotide sequence which is 95% identical to SEQ ID NO: 2, wherein said polynucleotide sequence encodes a polypeptide having the activity of polyphosphate:AMP phosphotransferase.
3. A vector comprising the isolated polynucleotide of claim 1.
4. A vector comprising the isolated polynucleotide of claim 2.
5. A transformed microorganism comprising the isolated polynucleotide of claim 1.
6. A transformed microorganism comprising the isolated polynucleotide of claim 2.
7. A method of making polyphosphate:AMP phosphotransferase, comprising culturing the transformed microorganism of claim 1 under conditions suitable for expressing the isolated polynucleotide and producing polyphosphate:AMP phosphotransferase.
8. A method of making polyphosphate:AMP phosphotransferase, comprising culturing the transformed microorganism of claim 2 under conditions suitable for expressing the isolated polynucleotide and producing polyphosphate:AMP phosphotransferase.
9. A method of producing a nucleoside diphosphate, comprising culturing the transformed microorganism of claim 1 under conditions suitable for expressing the isolated polynucleotide and producing polyphosphate:AMP phosphotransferase;

collecting the polyphosphate:AMP phosphotransferase;

contacting nucleoside monophosphate with the polyphosphate:AMP phosphotransferase in the presence of polyphosphate as a phosphate donor to produce the nucleoside diphosphate.

10. A method of producing a nucleoside diphosphate, comprising culturing the transformed microorganism of claim 2 under conditions suitable for expressing the isolated polynucleotide and producing-polyphosphate:AMP phosphotransferase;

collecting the polyphosphate:AMP phosphotransferase;

contacting nucleoside monophosphate with the polyphosphate:AMP phosphotransferase in the presence of polyphosphate as a phosphate donor to produce the nucleoside diphosphate.

* * * * *

SEQUENCE LISTING

<160> NUMBER OF SEQ ID NOS: 2

<210> SEQ ID NO 1
<211> LENGTH: 475
<212> TYPE: PRT
<213> ORGANISM: Acinetobacter johnsonii

<400> SEQUENCE: 1

```
Met Asp Thr Glu Thr Ile Ala Ser Ala Val Leu Asn Glu Glu Gln Leu
1               5                   10                  15

Ser Leu Asp Leu Ile Glu Ala Gln Tyr Ala Leu Met Asn Thr Arg Asp
            20                  25                  30

Gln Ser Asn Ala Lys Ser Leu Val Ile Leu Val Ser Gly Ile Glu Leu
        35                  40                  45

Ala Gly Lys Gly Glu Ala Val Lys Gln Leu Arg Glu Trp Val Asp Pro
    50                  55                  60

Arg Phe Leu Tyr Val Lys Ala Asp Pro Pro His Leu Phe Asn Leu Lys
65                  70                  75                  80

Gln Pro Phe Trp Gln Pro Tyr Thr Arg Phe Val Pro Ala Glu Gly Gln
                85                  90                  95

Ile Met Val Trp Phe Gly Asn Trp Tyr Gly Asp Leu Leu Ala Thr Ala
            100                 105                 110

Met His Ala Ser Lys Pro Leu Asp Asp Thr Leu Phe Asp Glu Tyr Val
        115                 120                 125
```

```
Ser Asn Met Arg Ala Phe Glu Gln Asp Leu Lys Asn Asn Val Asp
    130                 135                 140

Val Leu Lys Val Trp Phe Asp Leu Ser Trp Lys Ser Leu Gln Lys Arg
145                 150                 155                 160

Leu Asp Asp Met Asp Pro Ser Glu Val His Trp Lys Leu His Gly
            165                 170                 175

Leu Asp Trp Arg Asn Lys Lys Gln Tyr Asp Thr Leu Gln Lys Leu Arg
            180                 185                 190

Thr Arg Phe Thr Asp Asp Trp Gln Ile Ile Asp Gly Glu Asp Glu Asp
            195                 200                 205

Leu Arg Asn His Asn Phe Ala Gln Ala Ile Leu Thr Ala Leu Arg His
    210                 215                 220

Cys Pro Glu His Glu Lys Lys Ala Ala Leu Lys Trp Gln Gln Ala Pro
225                 230                 235                 240

Ile Pro Asp Ile Leu Thr Gln Phe Glu Val Pro Gln Ala Glu Asp Ala
                245                 250                 255

Asn Tyr Lys Ser Glu Leu Lys Lys Leu Thr Lys Gln Val Ala Asp Ala
                260                 265                 270

Met Arg Cys Asp Asp Arg Lys Val Val Ile Ala Phe Glu Gly Met Asp
            275                 280                 285

Ala Ala Gly Lys Gly Gly Ala Ile Lys Arg Ile Val Lys Lys Leu Asp
    290                 295                 300

Pro Arg Glu Tyr Glu Ile His Thr Ile Ala Ala Pro Glu Lys Tyr Glu
305                 310                 315                 320

Leu Arg Arg Pro Tyr Leu Trp Arg Phe Trp Ser Lys Leu Gln Ser Asp
                325                 330                 335

Asp Ile Thr Ile Phe Asp Arg Thr Trp Tyr Gly Arg Val Leu Val Glu
            340                 345                 350

Arg Val Glu Gly Phe Ala Thr Glu Val Glu Trp Gln Arg Ala Tyr Ala
    355                 360                 365

Glu Ile Asn Arg Phe Glu Lys Asn Leu Ser Ser Ser Gln Thr Val Leu
370                 375                 380

Ile Lys Phe Trp Leu Ala Ile Asp Lys Asp Glu Gln Ala Ala Arg Phe
385                 390                 395                 400

Lys Ala Arg Glu Ser Thr Pro His Lys Arg Phe Lys Ile Thr Glu Glu
                405                 410                 415

Asp Trp Arg Asn Arg Asp Lys Trp Asp Asp Tyr Leu Lys Ala Ala Ala
            420                 425                 430

Asp Met Phe Ala His Thr Asp Thr Ser Tyr Ala Pro Trp Tyr Ile Ile
            435                 440                 445

Ser Thr Asn Asp Lys Gln Gln Ala Arg Ile Glu Val Leu Arg Ala Ile
    450                 455                 460

Leu Lys Gln Leu Lys Ala Asp Arg Asp Thr Asp
465                 470                 475

<210> SEQ ID NO 2
<211> LENGTH: 1847
<212> TYPE: DNA
<213> ORGANISM: Acinetobacter johnsonii

<400> SEQUENCE: 2
atggatacag aaacgatcgc cagtgcagtg ctgaatgaag aacagctttc actggactta      60
attgaagcgc aatatgcgtt gatgaatacc cgtgatcaga gcaatgcaaa aagtttagtg     120
```

-continued

```
attttggtca gtggaatcga acttgcgggt aaaggcgaag cggtgaaaca gctccgcgaa      180
tgggtcgatc ctcgtttttt atatgtcaaa gccgatccac cgcatctgtt taatctaaaa      240
cagccttttt ggcagcccta tacccgattt gtgcctgccg aagggcaaat tatggtgtgg      300
tttggtaatt ggtatgggga tttgttggct acggccatgc atgcttcaaa gcctttagat      360
gacactttgt ttgatgaata cgtcagcaat atgcgggctt ttgaacagga cttaaaaaat      420
aacaacgtag atgtcttaaa agtttggttc gatttgtcgt ggaagtctct gcaaaagcgt      480
ctagatgata tggacccgag cgaagtgcat tggcataagt tgcatgggct agactggcgc      540
aataaaaaac aatatgacac cttacaaaag ctacgtacgc gcttcaccga tgactggcaa      600
atcattgatg gtgaagatga ggatttgcgt aatcacaatt ttgcacaagc aattttaacg      660
gcactacgac actgcccaga gcatgaaaaa aaggccgcgc taaatggca gcaagcacca       720
ataccagata ttctgactca gtttgaagtc cctcaagctg aggatgcgaa ctataaatca      780
gaattgaaaa aactcaccaa acaagtggcc gatgccatgc gctgtgatga ccgtaaagtg      840
gtgattgctt ttgaaggtat ggatgctgcg ggtaaagggg gggcgattaa gcgtattgtg      900
aaaaagctcg acccacgaga atatgaaatt cataccattg ccgcacctga aaaatatgag      960
ttacgccgtc cttatctgtg gcgttttggg agcaaattgc agtcggatga catcactatt     1020
tttgatcgga cgtggtatgg acgcgtttta gtcgagcggg tagaaggctt cgcaaccgag     1080
gtagagtggc aacgcgctta tgcggaaatc aatcgttttg aaaaaaacct cagtagcagc     1140
caaaccgtgc tgattaagtt ttggctggcg attgataaag atgaacaagc agcgcgtttt     1200
aaagcccgcg aaagtactcc gcataaacgt tttaaaatta ccgaagaaga ttggcgcaat     1260
cgcgacaaat gggatgacta tttaaaggca gccgcggata tgtttgcgca taccgacacc     1320
agctatgcgc cttggtatat tatttccacc aatgataaac aacaggcccg cattgaagtc     1380
ttaagggcaa ttttaaaaca gctcaaagcg gatcgcgaca cggattaaaa aaattaaaaa     1440
aaaacggtca tttgaccgtt ttttatagag gcagatttag tttttttaact taagggaatt     1500
tgggtcactg gcgctgcaac aggaacacct tgttcagcgg cttgttttag ttgaatgcct     1560
ttggcgagct tatacgactc ttccacatgg gttttccgcaa ttttttttcat cacgacataa    1620
cccaagctgg ccgcaatcat ttgtccacct aagggaataa atttagtgac ttgttttggta    1680
atgaatttgg ctgccatgtt attgatggat tttttcacgg ctgtacgtgc gaccaccagt     1740
ccagagaact ccacaccacg tttacgcagt tctgaccaat gtatttgctt agtttctggg     1800
tcgtagacac tgacttgctc aggggttaaa ccaaagcggg cgttaac                   1847
```